US008333728B2

(12) United States Patent
Bertrand et al.

(10) Patent No.: US 8,333,728 B2
(45) Date of Patent: Dec. 18, 2012

(54) IMPLANTABLE CEREBROSPINAL FLUID FLOW DEVICE AND METHOD OF CONTROLLING FLOW OF CEREBROSPINAL FLUID

(75) Inventors: William J. Bertrand, Ventura, CA (US); Lori C. Speckman, Ventura, CA (US); Javier J. Reveles, Goleta, CA (US); Andy R. Kiehl, Oakview, CA (US)

(73) Assignee: Medtronic, Inc., Minneapolis, MN (US)

( * ) Notice: Subject to any disclaimer, the term of this patent is extended or adjusted under 35 U.S.C. 154(b) by 571 days.

(21) Appl. No.: 11/605,936

(22) Filed: Nov. 29, 2006

(65) Prior Publication Data

US 2007/0129663 A1 Jun. 7, 2007

Related U.S. Application Data

(60) Provisional application No. 60/741,118, filed on Dec. 1, 2005.

(51) Int. Cl.
| | |
|---|---|
| *A61M 5/00* | (2006.01) |
| *A61M 39/00* | (2006.01) |
| *A61M 29/00* | (2006.01) |
| *A61M 25/00* | (2006.01) |
| *A61M 25/14* | (2006.01) |
| *A61F 2/02* | (2006.01) |
| *A61F 2/04* | (2006.01) |
| *A61F 2/82* | (2006.01) |

(52) U.S. Cl. ............ 604/9; 604/8; 604/10; 604/27; 604/28; 604/540; 604/43; 604/523; 604/93.01; 623/1.1; 623/1.34

(58) Field of Classification Search ............ 623/1.1; 128/898; 137/455, 511, 512, 802; 604/173, 604/175, 264, 272, 8–10, 27, 28, 540, 43, 604/523, 93.01

See application file for complete search history.

(56) References Cited

U.S. PATENT DOCUMENTS

| | | | | |
|---|---|---|---|---|
| 3,623,484 | A | * | 11/1971 | Schulte .................. 604/8 |
| 3,654,932 | A | * | 4/1972 | Newkirk et al. ............ 604/9 |
| 3,690,323 | A | * | 9/1972 | Wortman et al. ............ 604/8 |
| 4,103,689 | A | * | 8/1978 | Leighton .................. 604/9 |
| 5,114,401 | A | * | 5/1992 | Stuart et al. ............. 604/510 |
| 5,511,965 | A | | 4/1996 | Batdorf et al. |
| 5,549,579 | A | | 8/1996 | Batdorf et al. |
| 5,658,221 | A | * | 8/1997 | Hougen ................. 482/13 |
| 5,728,061 | A | * | 3/1998 | Ahmed ................. 604/9 |
| 5,738,666 | A | | 4/1998 | Watson et al. |
| 5,792,660 | A | * | 8/1998 | Spillert et al. ............. 436/2 |
| 5,945,052 | A | | 8/1999 | Schryver et al. |

(Continued)

OTHER PUBLICATIONS

Sherwood, Lauralee. Fundamentals of Physiology: A Human Perspective. 2005. ISBN:0534466974. (p. 289-291).*
Online encyclopedia article "Potentiometer—Wikipedia" accessed Tuesday, Jun. 30, 2009. http://en.wikipedia.org/wiki/Potentiometer.*
Bloomfield et al., "Effects of Proteins, Blood Cells and Glucose on the Viscosity of Cerebrospinal Fluid." Pediatric Neurosurgery 1998;28:246-251. Accessed Tuesday, Jun. 30, 2009. http://content.karger.com/ProdukteDB/produkte.asp?Aktion=ShowAbstract&ArtikelNr=28659&Ausgabe=226483&ProduktNr=224273.*

(Continued)

*Primary Examiner* — Leslie Deak
*Assistant Examiner* — Adam Marcetich
(74) *Attorney, Agent, or Firm* — IPLM Group, P.A.

(57) ABSTRACT

An implantable shunt that includes one or more catheters configured so that the implantable shunt has a resistance to flow greater than about 3 mm Hg/mL/minute. An implantable shunt system that includes one or more catheters and a fluid control device that utilizes the properties of the catheters to improve the expected function of the shunt by providing a higher or lower resistance to the flow through the shunt and reduces the effect of pulsations of cerebrospinal fluid on the shunt system.

12 Claims, 6 Drawing Sheets

U.S. PATENT DOCUMENTS

| | | | |
|---|---|---|---|
| 6,083,141 A * | 7/2000 | Hougen | 482/13 |
| 6,162,975 A * | 12/2000 | Purdue | 84/395 |
| 6,283,934 B1 * | 9/2001 | Børgesen | 604/9 |
| 6,394,141 B2 | 5/2002 | Wages et al. | |
| 2002/0045847 A1 * | 4/2002 | Borgesen | 604/9 |
| 2002/0128588 A1 * | 9/2002 | Borgesen | 604/9 |
| 2003/0221606 A1 * | 12/2003 | Quigley et al. | 116/286 |
| 2005/0010159 A1 * | 1/2005 | Reich et al. | 604/8 |
| 2005/0055009 A1 * | 3/2005 | Rosenberg | 604/500 |
| 2005/0085763 A1 * | 4/2005 | Ginggen et al. | 604/9 |
| 2005/0085764 A1 * | 4/2005 | Borgesen | 604/9 |
| 2005/0096580 A1 * | 5/2005 | Moskowitz et al. | 604/9 |
| 2006/0090753 A1 * | 5/2006 | Pelerossi et al. | 128/200.24 |

OTHER PUBLICATIONS

Online article "How Does a Potentiometer Work?—eHow.com" accessed Tuesday, Jun. 30, 2009. http://www.ehow.com/how-does_4911354_a-potentiometer-work.html.*

"indicia." Merriam-Webster Online Dictionary. 2010. Merriam-Webster Online. Jan. 28, 2010. <http://www.merriam-webster.com/dictionary/indicia>.*

Czosnyka, Z. H. et al., "Hydrocephalus shunts and waves of intracranial pressure", Med. Bio. Eng. Comput. Jan. 2005 43(1) 71-7.

"Specialty Silicone Fabricators", www.ssfab.com, 2005, 6 pgs.

* cited by examiner

IMPLANTABLE CEREBROSPINAL FLUID FLOW DEVICE AND METHOD OF CONTROLLING FLOW OF CEREBROSPINAL FLUID

RELATED APPLICATION

This application is related to and claims priority from U.S. Patent Application Ser. No. 60/741,118, filed Dec. 1, 2005.

FIELD

This invention relates generally to implantable fluid flow control devices and methods and, more particularly, to such devices and methods for controlling flow of cerebrospinal fluid.

BACKGROUND

Ventricles of the brain contain cerebrospinal fluid which cushions the brain against shock and provides a means for nutrient and waste transport in the brain. Cerebrospinal fluid is constantly being secreted and absorbed by the body, usually in equilibrium. Cerebrospinal fluid is produced in the ventricles of the brain, where under normal conditions, it is circulated in the subarachnoid space and reabsorbed into the bloodstream, predominantly into the superior sagittal sinus via the arachnoid villi. However, if blockages exist in the circulation pathways of cerebrospinal fluid, perhaps in the ventricles, cerebrospinal fluid can't be reabsorbed by the body at the proper rate.

This imbalance can create a condition known as hydrocephalus: a condition marked by an excessive accumulation of fluid in subarachnoid space, including the cerebral ventricles. Hydrocephalus is a condition characterized by abnormal flow, absorption or formation of cerebrospinal fluid which may subsequently increase the volume and/or pressure of the intracranial cavity. If left untreated, the increased intracranial pressure can lead to neurological damage and may result in death.

Over the past 40 years, a common treatment for hydrocephalus patients has been the cerebrospinal fluid shunt. A standard shunt consists of the proximal (upstream) catheter, a valve and a distal (downstream or discharge) catheter. The excess cerebrospinal fluid is typically drained from the ventricles or other subarachnoid location to a suitable cavity, most often the peritoneum or the right atrium of the heart. A ventricular catheter is inserted into the brain through a burr hole in the skull. Alternatively, the proximal catheter can be placed between the vertebrae into the spinal subarachnoid space. The catheter placed into the subarachnoid space shunts cerebrospinal fluid to other areas of the body, where it can be reabsorbed. The presence of the shunt relieves pressure from cerebrospinal fluid on the brain.

A common complication for these implanted shunt systems is over-drainage, potentially resulting in slit ventricles, slit ventricle syndrome, loss of brain compliance, shunt occlusion, sub-dural hematoma or any of a number of other complications. Current methods for addressing this issue include the use of adjustable valves such as the STRATA™ and STRATA NSC™ valves (STRATA and STRATA NSC are trademarks of Medtronic, Inc., Minneapolis, Minn.). Over-drainage may still occur with the use of these valves due to significant intracranial pressure spikes.

Shunt valves are also prone to clogging. A clogged shunt valve could result in serious complications through failure to provide proper drainage of cerebrospinal fluid from the ventricles of the brain. Therefore it is desirable to avoid narrow passageways within the shunt system which could increase the incidence of shunt clogging and occlusion.

SUMMARY

The invention provides an implantable shunt that includes one or more catheters configured so that the implantable shunt has a resistance to flow greater than about 3 mm Hg/mL/minute. In one embodiment, the one or more catheters includes the distal catheter. In another embodiment, the resistance to flow is a function of the cross section and the length of the one or more catheters.

The invention provides an implantable shunt system that includes one or more catheters and a fluid control device that utilizes the properties of the catheters to improve the expected function of the shunt by providing a higher or lower resistance to the flow through the shunt and reducing the effect of pulsations of intracranial pressure on the shunt system.

In one embodiment, the resistance to flow and pulsations is controlled at least in part by changing the length of the tubing. In another embodiment, the resistance to flow and pulsations is controlled at least in part by the internal dimensional properties of the catheter.

One embodiment of the invention also includes integral fittings that allow connection of catheters in accordance with the invention with commercially available or commonly used shunt components, such as valves.

DRAWINGS

DETAILED DESCRIPTION

The entire content of U.S. Patent Application Ser. No. 60/741,118, filed Dec. 1, 2005, is hereby incorporated by reference.

Consistent and reliable drainage of cerebrospinal fluid from one area of the body to another, e.g., from a ventricle or ventricles of the brain to another region of the body such as the peritoneum or sagittal sinus, can be desirable. A consistent and reliable drainage method and system can minimize the expense as well as trauma and inconvenience to the patient associated with cerebrospinal fluid shunt revision surgery and can also lessen risk to the patient due to an inoperative cerebrospinal fluid drainage system.

Figure 1:
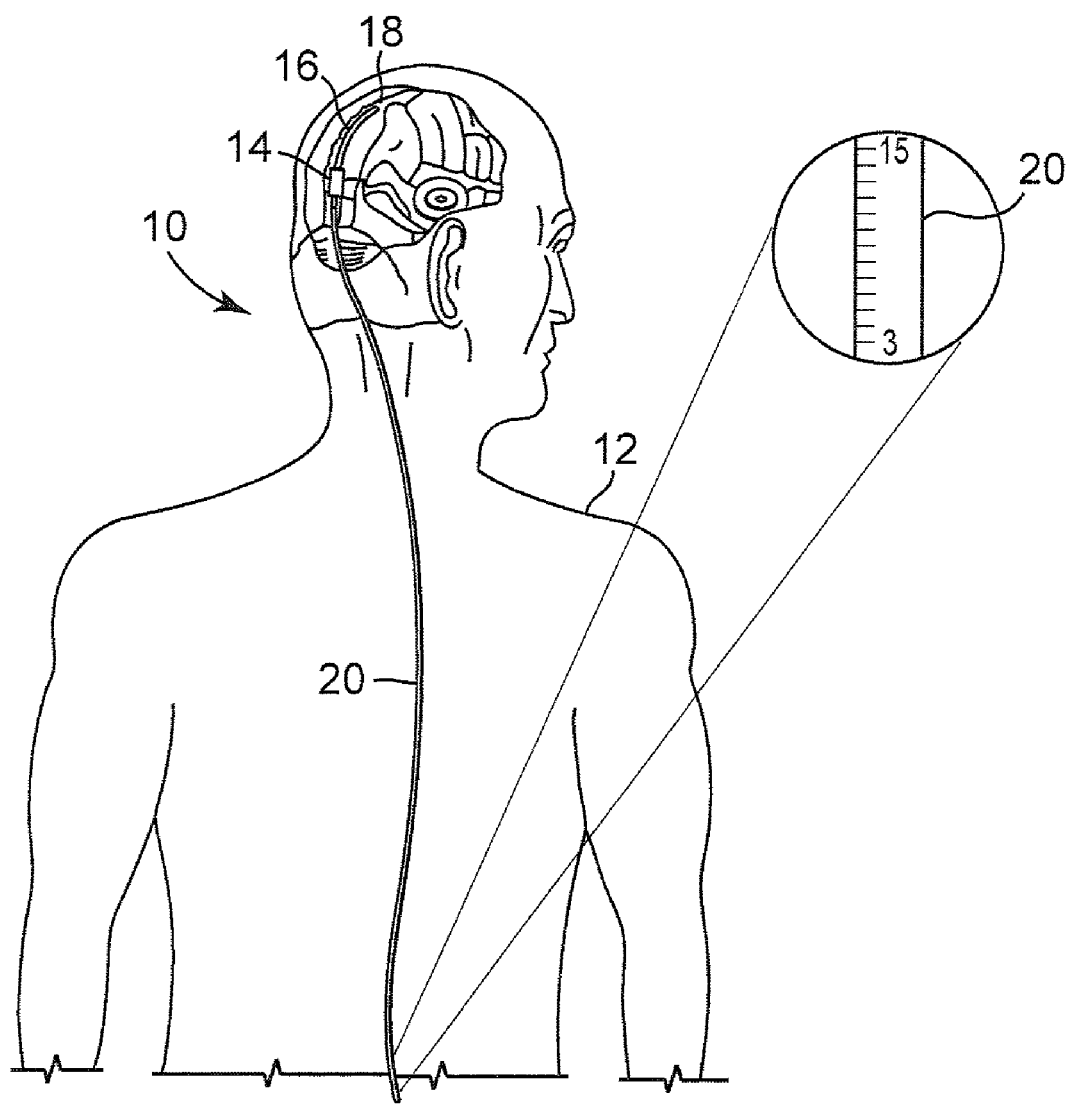
FIG. 1 is a cut-away perspective view of cerebrospinal fluid flow control device implanted into the cranium of a patient.

FIG. 1 illustrates an embodiment of a cerebrospinal fluid shunt 10 for draining cerebrospinal fluid from one area, for example the ventricles of the brain, of the body of patient 12 to another area of the body of patient 12. In one embodiment cerebrospinal fluid can be drained to the peritoneum, the right atrium, the sagittal sinus, or some combination thereof. A cerebrospinal fluid shunt 10 in accordance with the invention includes one or more catheters that are configured to give the cerebrospinal fluid shunt 10 a resistance to flow greater than about 3 mm Hg/ml/minute. In another embodiment of the invention, a cerebrospinal fluid shunt 10 in accordance with the invention includes one or more catheters that are configured to give the cerebrospinal fluid shunt 10 a resistance to flow between about 3 mm Hg/ml/minute and 15 mm Hg/ml/minute. In yet another embodiment of the invention, a cerebrospinal fluid shunt 10 in accordance with the invention includes one or more catheters that are configured to give the cerebrospinal fluid shunt 10 a resistance to flow between about 3 mm Hg/ml/minute and 10 mm Hg/ml/minute.

In one embodiment, the one or more catheters that are configured to give the cerebrospinal fluid shunt 10 a resistance to flow greater than about 3 mm Hg/ml/minute includes the distal catheter 20. In another embodiment, the one or more catheters that are configured to give the cerebrospinal fluid shunt 10 a resistance to flow greater than about 3 mm Hg/ml/minute includes the ventricular catheter 16. In yet another embodiment, both the distal catheter 20 and the ventricular catheter 16 are configured to give the cerebrospinal fluid shunt 10 a resistance to flow greater than about 3 mm Hg/ml/minute.

Another embodiment includes a fluid control device 14. Fluid control device 14 may be located anywhere along the path of cerebrospinal fluid flow. For example, fluid control device 14 may be located at or near the inlet for cerebrospinal fluid, e.g., at or near the ventricles, or may be located at or near the outlet for the cerebrospinal fluid, e.g., at or near the peritoneum. Alternatively, fluid control device 14 may be located as illustrated in FIG. 1 along the flow path between the inlet and outlet. In particular, by way of example, fluid control device 14 may be near the cranium of the patient. Examples of possible devices that may be used as fluid control device 14 in embodiments of the invention include, but are not limited to Medtronic's STRATA NSC Valve, STRATA Valve, and DELTA Valve, among others.

Ventricular catheter 16 includes an inlet location 18 in the ventricle of patient 12. It is to be recognized and understood that other locations or configurations, other than inlet location 18, can be utilized for entry of cerebrospinal fluid into the cerebrospinal fluid shunt 10 including the lumbar region. Distal catheter 20 includes an outlet for cerebrospinal fluid, not shown, which in one embodiment of the invention is in the peritoneum. It is to be recognized and understood that other outlet locations can be used. Examples of other possible outlet locations include the right atrium and the sagittal sinus.

The one or more catheter of the cerebrospinal fluid shunt 10 is configured to cause the resistance of the cerebrospinal fluid shunt 10 to have a resistance greater than about 3 mm Hg/ml/minute. The catheter can be configured by adapting the cross section, the inner diameter, the length of the catheter, or some combination thereof.

In one embodiment, the geometry of the one or more catheters is adapted to increase the resistance to flow. Generally, the specific geometry can include any geometry that has a greater resistance to flow than does a cylindrical geometry.

Examples of possible geometries that could be utilized include, but are not limited to a convoluted pathway, a labyrinth, a tapered inner diameter, a variable inner diameter, one or more flow paths within the outer geometry, or some combination thereof. One of skill in the art, having read this specification, would know how the one or more catheters with adapted geometries could be manufactured. One example of an adapted geometry could include a spiral interior lumen within a cylindrical outside geometry. The spiral flow path would effectively increase the length of the flow path thereby increasing the overall geometry. More than one spiral flow path could also be included within a cylindrical outside geometry. Such a configuration would both increase the length of the flow path and could decrease the diameter of the independent paths. An example of a technology that could be used to manufacture adapted geometry tubing for medical device applications is used by the company Specialty Silicone Fabricators (Paso Robles, Calif.). Exemplary tubing that can be manufactured using their technology can be seen on their website www.ssfab.com. Examples of particular geometries that can be fabricated and particular methods of fabricating can be found in the following, the disclosure of which is incorporated herein by reference: U.S. Pat. Nos. 5,549,579; 5,511,965; 5,945,052; and 6,394,141. Another example of a possible geometry for a flow path may include hourglass shapes.

Figure 2A:
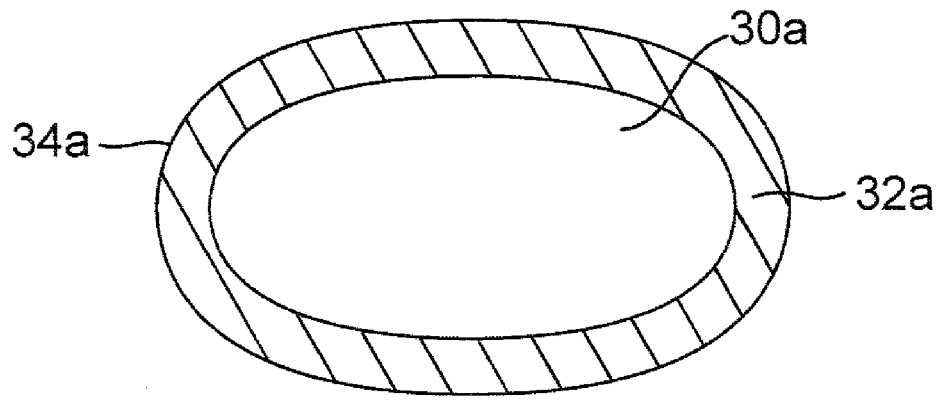
FIG. 2a is an example of a possible cross section of a catheter.
Figure 2B:
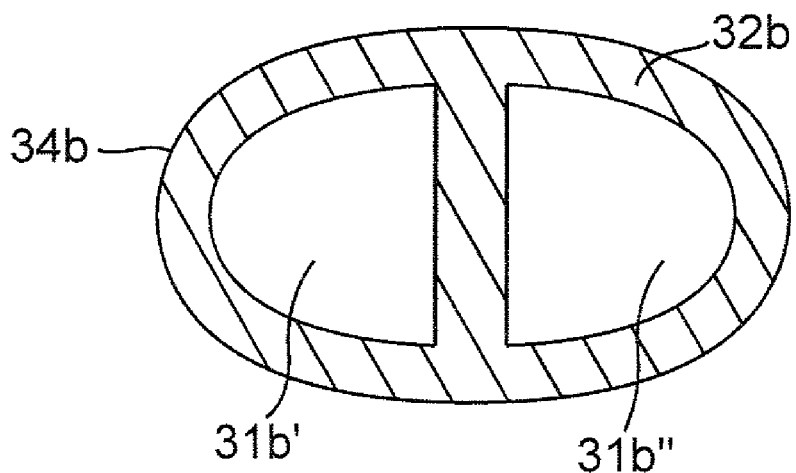
FIG. 2b is another example of a possible cross section of a catheter.
Figure 2C:
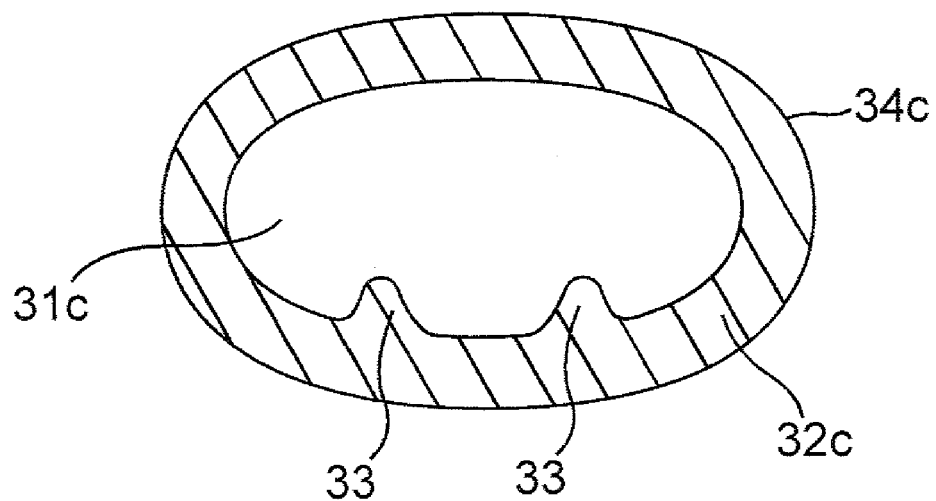
FIG. 2c is another example of a possible cross section of a catheter.
Figure 2D:
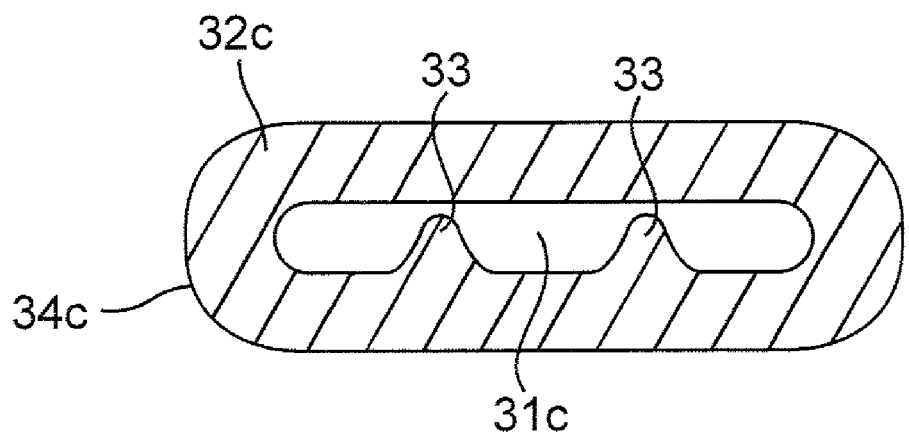
FIG. 2d is another example of a possible cross section of a catheter.

Other ways of adapting the cross section of the one or more catheter could include a consideration of the outside diameter. In one embodiment it may be desirable to have an elliptically shaped outside diameter of the one or more catheters. It may be desirable to have an elliptically shaped outside diameter of the one or more catheters because it may be more comfortable to the patient and/or be more cosmetically acceptable to the patient. An example of such geometry is depicted in FIG. 2a. The catheter depicted in FIG. 2a is ellipsoid, and includes a lumen 30a, and a tube 32a having an ellipsoid profile 34a. This exemplary cross section would increase the resistance to flow, when compared to a cylindrical catheter having the same internal volume. However, such a catheter may provide increased comfort to the patient, a more acceptable cosmetic appearance and be less likely to collapse than a cylindrical catheter having the same internal volume. FIG. 2b offers another example of an adapted cross section. This example of a catheter includes a tube 32b, two lumens 31b' and 31b" and an ellipsoid profile 34b. Another example of a catheter with an adapted cross section is depicted in FIG. 2c. This catheter includes a tube 32c, a lumen 31c, and an ellipsoid profile 34c. The tube 32c in this example includes two bumps 33. The bumps 33 can serve to stop the catheter from completely collapsing and occluding the catheter. FIG. 2d depicts this catheter in a collapsed state and shows that the bumps 33 stop the tube 32c from completely collapsing.

In one embodiment, the inner diameter of the one or more catheter(s) is adapted. In such an embodiment, the one or more catheters are generally cylindrical in shape. In one embodiment, the inner diameter of the one or more cylindrical catheters is adapted to increase the resistance to flow. As the inner diameter of the one or more catheters is decreased, the resistance to flow is increased.

One example of a distal catheter that is commonly used in prior art cerebrospinal fluid shunts is a PS MEDICAL® Peritoneal Catheter. These catheters are commercially available for example with the following dimensions: outer diameter 0.100 inches (0.25 cm), inner diameter 0.050 inches (0.13 cm); outer diameter 0.084 inches (0.21 cm), inner diameter 0.046 inches (0.12 cm); and outer diameter 0.059 inches (0.15 cm) and inner diameters 0.028 inches (0.07 cm). The 0.028" (0.07 cm)×0.059" (0.15 cm) catheter tubing provides increased resistance to flow relative to larger inner diameter peritoneal catheters, but is not amenable to direct connection to CSF fluid control devices which typically include barbed connectors with outer diameters of approximately 0.090" (0.23 cm). Due to its smaller inner diameter, the 0.028" (0.07 cm)×0.059" (0.15 cm) catheter tubing is typically connected to Medtronic's STRATA and STRATA NSC valves via a step-down connector. One side of the step-down connector accommodates 0.050" (0.13 cm)×0.100" (0.25 cm) diameter catheter tubing which is connected to the valve, and the other, smaller side of the connector accommodates the 0.028" (0.07 cm)×0.059" (0.15 cm) catheter tubing. Use of such a connector in the CSF shunt system can prolong surgery time and therefore expense, and also creates a stress point potentially leading to catheter tubing rupture and leakage. The embodiments of this patent exhibit an integral adaptor to the tubing which allows for the direct connection of small-lumen catheters, non-cylindrical lumen catheters, large-lumen catheters or multi-lumen catheters to a standard connector generally used in shunt components.

Figure 3:
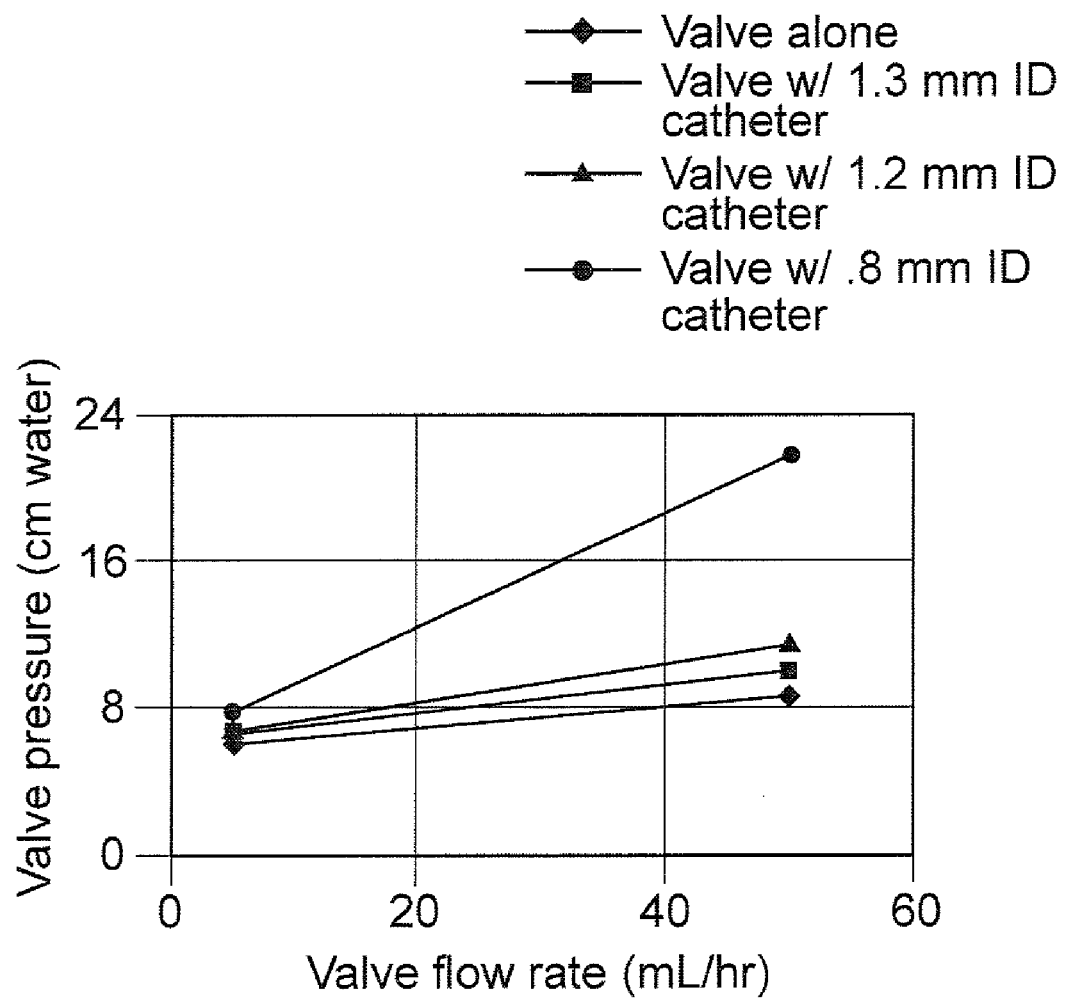
FIG. 3 depicts the variation of the flow rate through a cerebrospinal fluid shunt in accordance with the invention.

FIG. 3 depicts the variation of the flow rate through a valve of a cerebral fluid spinal shunt in accordance with the invention. The cerebrospinal fluid shunts that are modeled in FIG. 3 have a single valve and a 90 cm distal catheter. A figure such as this can be used to model the resistance to flow of a cerebrospinal fluid shunt in accordance with the invention, to determine the particular inner diameter that is desired to provide a desired resistance to flow.

In one embodiment, the length of the one or more catheter(s) is adapted. A catheter having any of the exemplary geometries discussed above could be modified by modifying the length of the catheter. In one such embodiment, the one or more catheters are generally cylindrical in shape. In one embodiment, the length of the one or more cylindrical catheters is adapted to increase the resistance to flow. As the length of the one or more catheters is increased, the resistance to flow is increased. In one embodiment where the length is adapted to increase the resistance to flow, the one or more catheters has a cylindrical geometry.

Another embodiment of a cerebrospinal fluid shunt in accordance with the invention has one or more catheters that are configured to be modified at the time of implant to provide a desired resistance to flow. Such catheters can be referred to as trimmable. Such an embodiment can be implanted and then cut to a desired length, or can be cut to the desired length before implantation. One embodiment includes a distal catheter that is trimmable. One such embodiment can include markings on the catheter that provide the resistance to flow that would be obtained if the catheter were trimmed at that point. The markings can be configured to provide a flow resistance of greater than about 3 mm Hg/ml/minute. In one embodiment, the markings are provided in increments of 1 mm Hg/ml/minute and range from 3 mm Hg/ml/minute until 15 mm Hg/ml/minute.

In one embodiment, both the length and inner diameter of the one or more catheters is configured to cause the resistance of the cerebrospinal fluid shunt 10 to have a resistance greater than about 3 mm Hg/ml/minute. In one embodiment, a desired resistance is determined, and then the length and inner diameter of the catheter is determined. In such an embodiment, it may be desired once the resistance is chosen to determine the length of the catheter that is wanted and then determine the inner diameter. The relationship of the resistance of flow to the length and the inner diameter is known from fluid dynamics.

The use of a cerebrospinal fluid shunt in accordance with the invention may be capable of dampening pulses in the intracranial pressure of a patient once the shunt is implanted. The response of valve operating pressures to varying amplitudes of simulated heart pulsations has been shown. *Med. Bio. Eng. Comput.* 2005 January; 43(1):71-7. For all valves tested, the valve operating pressure decreased with increasing amplitude of pulsations. The magnitude of the drop was different for different valves. Cerebrospinal fluid shunts in accordance with the invention, with higher resistance to flow, compared to the valves and systems tested, may result in a decreased effect of simulated heart pulsations on the valve operating pressure.

One embodiment of a cerebrospinal fluid shunt in accordance with the invention can include commercially available components that are commonly utilized for cerebrospinal fluid shunting. Examples of such components include, but are not limited to fluid control devices such as valves. In such an embodiment, commercially available valves, previously described valves, or combinations thereof. Examples of these valves can include Medtronic's STRATA NSC Valve, STRATA Valve, DELTA valve, and others. A description of one such valve can be found in U.S. Pat. No. 5,738,666, the disclosure of which is incorporated herein by reference. Cerebrospinal fluid shunts that include commercially available or commonly known components, such as valves, can also include one or more fittings that allow the one or more catheters of the invention to interface with the commercially available or commonly known components without modifying those components.

In one embodiment, the one or more fitting can be an integral part of the one or more catheter that is configured to provide a resistance to flow that is greater than about 3 mm Hg/ml/minute. An example of an integral fitting can be seen in FIG. 4.

Figure 4:
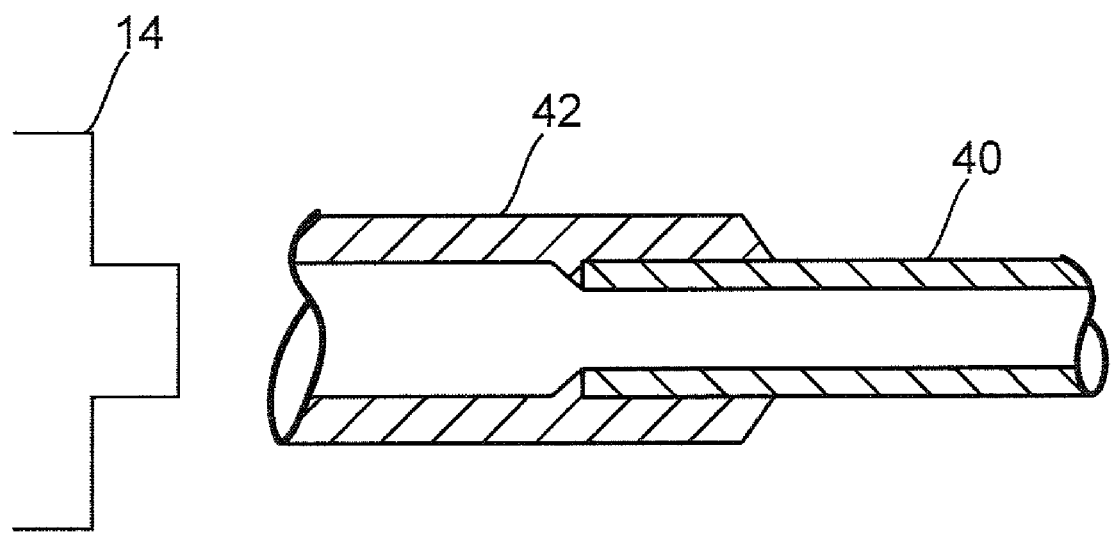
FIG. 4 depicts an example of an integral fitting in accordance with an embodiment of the invention.

FIG. 4 shows the catheter 40 (which could be either the distal catheter 20 or ventricular catheter 16 as shown in FIG. 1), with the integral fitting 42, which connects it to the fluid control device 14. This embodiment depicts a catheter 40 that has a decreased inner diameter to increase the resistance to flow. It should also be understood by one of skill in the art, having read this specification, that an integral fitting could also be utilized in a catheter that has been configured by modifying the geometry of the catheter. Such an embodiment would, at the end of the catheter 40 that is connecting to the fluid control device 14, be manufactured such that the inner diameter and cross section of the catheter 40 are modified from the geometry of the catheter 40 to that of the fluid control device 14.

It will also be understood by one of skill in the art, having read this specification, that the example depicted in FIG. 4 showing that the integral fitting 42 makes a smooth transition from the catheter 40 inner diameter to a catheter that will fit onto the fluid control device 14 without modifying the flow control device 14 itself is only one exemplary method of creating the integral fitting.

Figure 5:
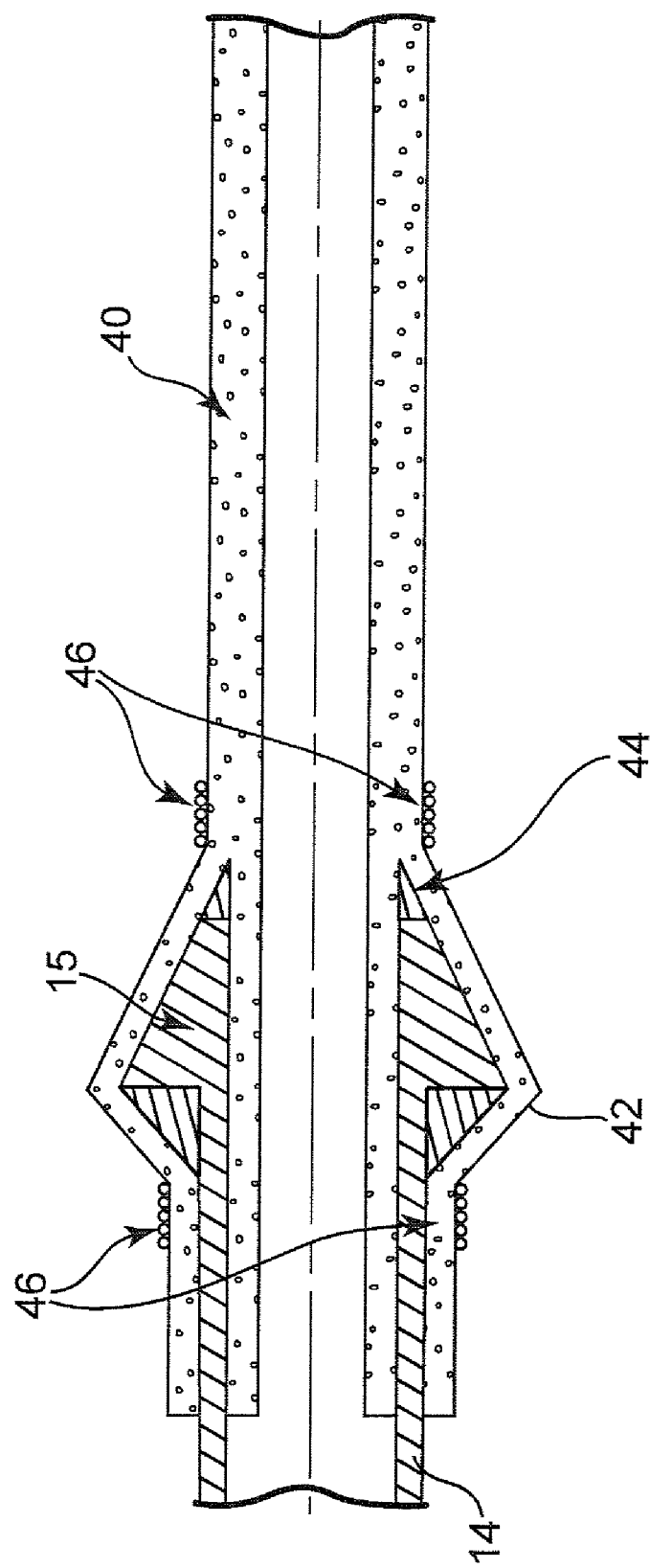
FIG. 5 depicts an example of an integral fitting in accordance with an embodiment of the invention.

FIG. 5 depicts another exemplary integral fitting that can be utilized in a cerebrospinal fluid shunt in accordance with the invention that incorporates a commercially available or commonly known cerebrospinal fluid shunt component, such as a valve. The integral fitting 42 depicted in FIG. 5 attaches the catheter 40 to the fluid control device 14 without modifying the fluid control device 14 and its barbed connector 15. Generally speaking, this integral fitting 42 functions to mirror and enclose the outside cross section of the barbed connector 15 in a portion of the wall of the catheter 40. This exemplary integral fitting 42 includes a portion of the catheter 40 that has a split wall. The split wall begins at the barb point 44 where the barbed connector 15 of the fluid control device 14 will sit when connected. The catheter 40 can alternatively be further attached to the fluid control device 14 with one or more sutures 46. One of ordinary skill in the art, having read this specification, would know how this split wall portion of the catheter 40 could be manufactured.

The split wall in the end of the catheter can be manufactured using a variety of methods. In one embodiment, the slit at the end of the catheter can be insert-molded on to the end of an existing catheter: the molded portion containing the slit around one end. In another exemplary embodiment, the inner diameter and/or the outer diameter of the catheter could be mechanically supported to reduce deformation. A mechanical means, such as a bit or a blade, could be used to slice a slit around the end of the catheter. The cutting action of the blade could use vibrations, or bluntly push into the end of the catheter forming the slit. In another embodiment, the tubing is co-extruded. The split in the end of the catheter is formed by separating the layers of the co-extruded catheter. Sutures 46 located at the terminus of the slit prevent it from propagating further down the catheter than desired.

A cerebrospinal fluid shunt in accordance with the invention can also include a fitting that is not integral with the body of the catheter tubing that is configured to increase the resistance to flow. Such a fitting could simply be manufactured and attached onto the one or more catheters with adhesive, insert molded or other methods as would be known to one of skill in the art having read this specification, thus creating a catheter assembly with integral fitting.

Thus, embodiments of the implantable cerebrospinal fluid flow device and method of controlling flow of cerebrospinal fluid are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable shunt, comprising:
    one or more catheters having a resistance to fluid flow, a catheter end and indicia disposed at locations along the one or more catheters, the indicia being indicative of a resistance to fluid flow should the catheter end be coincident with the indicia at a particular location along the one more or more catheters.

2. The implantable shunt according to claim 1 wherein each of the one or more catheters have a primarily tubular outer geometry, having an inlet at one end of the primarily tubular outer geometry and an outlet at another end of the primarily tubular outer geometry, and having a primarily longitudinal fluid flow from the inlet to the outlet;
    the one or more catheters having an inner geometry with an interior geometrical element being formed longitudinally along the inner geometry;
    the inner geometry being configured so that the implantable shunt has a resistance to flow greater than about 3 mm Hg/mL/minute.

3. The implantable shunt according to claim 2 wherein the one or more catheters comprises a ventricular catheter.

4. The implantable shunt according to claim 2 wherein the one or more catheters comprises a distal catheter.

5. The implantable shunt according to claim 2 further comprising a fluid control device operatively coupled to the one or more catheters.

6. The implantable shunt according to claim 5 further comprising an integral fitting that connects the fluid control device to the one or more catheters.

7. The implantable shunt according to claim 6 wherein the one or more catheters further comprises an integral fitting that connects the one or more catheters to the fluid control device.

8. The implantable shunt according to claim 2 wherein the inner geometry provides the greater resistance to fluid flow at least in part because of an increase in surface area relative to the outer geometry.

9. The implantable shunt according to claim 2 wherein the outer geometry is cylindrical.

10. The implantable shunt according to claim 1 which has a resistance to flow greater than about 3 mm Hg/mL/minute.

11. The implantable shunt according to claim 1 which has a resistance to flow greater than about 5 mm Hg/mL/minute.

12. The implantable shunt according to claim 1 wherein the indicia are marks.

* * * * *